United States Patent
Lapp et al.

(10) Patent No.: US 12,303,252 B2
(45) Date of Patent: May 20, 2025

(54) COMPUTER-IMPLEMENTED METHOD FOR CLASSIFYING A BODY TYPE

(71) Applicant: Siemens Healthcare GmbH, Erlangen (DE)

(72) Inventors: Robert Lapp, Nuremberg (DE); Andreas Prokein, Bubenreuth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 38 days.

(21) Appl. No.: 17/315,543

(22) Filed: May 10, 2021

(65) Prior Publication Data

US 2021/0353176 A1 Nov. 18, 2021

(30) Foreign Application Priority Data

May 18, 2020 (DE) ...................... 10 2020 206 232.3

(51) Int. Cl.
*A61B 5/107* (2006.01)
*A61B 5/00* (2006.01)
*G06T 7/00* (2017.01)

(52) U.S. Cl.
CPC .......... *A61B 5/1079* (2013.01); *A61B 5/0064* (2013.01); *A61B 5/4872* (2013.01);
(Continued)

(58) Field of Classification Search
CPC ... A61B 5/1079; A61B 5/0064; A61B 5/4872; A61B 5/7264; A61B 5/1077;
(Continued)

(56) References Cited

U.S. PATENT DOCUMENTS 10,621,779 B1 * 4/2020 Topiwala ................. G06N 3/08
10,813,715 B1 * 10/2020 Chojnowski .......... G06F 3/0304
(Continued)

FOREIGN PATENT DOCUMENTS

WO WO 2009035235 A1 3/2009

OTHER PUBLICATIONS

Guidi et al., "A support vector machine tool for adaptive tomotherapy treatments: Prediction of head and neck patients criticalities", 2015, Physica 31, pp. 442-451 (Year: 2015).*
(Continued)

*Primary Examiner* — Adil Partap S Virk
(74) *Attorney, Agent, or Firm* — Harness, Dickey & Pierce, P.L.C.

(57) ABSTRACT

A computer-implemented method is for classifying a body type of at least one person. In an embodiment, the method includes receiving at least one image data record of the respective person, which maps at least one subarea of the person; and ascertaining a body type for the person by an optimization method. A respective person model is used for each of the possible body types, which as a function of at least one person parameter determines an expected person geometry of the person described by the person model. The body type is selected by the optimization method by a similarity measure for the similarity of the image data record or a person geometry ascertained from the image data record being optimized with the expected person geometry by selecting the body type.

19 Claims, 3 Drawing Sheets

(52) U.S. Cl.
CPC .......... *A61B 5/7264* (2013.01); *G06T 7/0012* (2013.01); *G06T 2207/10081* (2013.01); *G06T 2207/10116* (2013.01); *G06T 2207/30196* (2013.01)

(58) Field of Classification Search
CPC ......... G06T 7/0012; G06T 2207/10081; G06T 2207/10116; G06T 2207/30196; G06T 7/73; G06T 2207/10072; G06T 2207/20081; G06T 2207/20084; G06T 2207/30004; G06T 7/62; G06K 9/6268; G06K 9/6218; G06K 9/6256; G06N 20/00; G16H 30/20
See application file for complete search history.

(56) References Cited

U.S. PATENT DOCUMENTS

| | | | | |
|---|---|---|---|---|
| 11,798,186 | B2* | 10/2023 | Barnes | G06T 7/62 |
| 2004/0116804 | A1* | 6/2004 | Mostafavi | A61B 6/541 |
| | | | | 600/428 |
| 2005/0207630 | A1* | 9/2005 | Chan | G06T 7/0012 |
| | | | | 382/131 |
| 2006/0008138 | A1* | 1/2006 | Zhou | G06V 10/7553 |
| | | | | 382/154 |
| 2009/0226060 | A1* | 9/2009 | Gering | G06T 7/174 |
| | | | | 382/128 |
| 2009/0318815 | A1* | 12/2009 | Barnes | A61B 5/444 |
| | | | | 382/128 |
| 2010/0111370 | A1* | 5/2010 | Black | G06F 18/2321 |
| | | | | 705/26.1 |
| 2010/0204622 | A1 | 8/2010 | Hwang et al. | |
| 2010/0260402 | A1* | 10/2010 | Axelsson | G06T 11/008 |
| | | | | 382/190 |
| 2012/0312961 | A1* | 12/2012 | Raleigh | A61B 6/542 |
| | | | | 250/206 |
| 2012/0316425 | A1* | 12/2012 | Raleigh | A61N 5/1049 |
| | | | | 600/407 |
| 2013/0250050 | A1* | 9/2013 | Kanaujia | H04N 13/106 |
| | | | | 348/42 |
| 2013/0287167 | A1* | 10/2013 | Gum | A61B 6/547 |
| | | | | 378/20 |
| 2013/0315475 | A1* | 11/2013 | Song | G06T 19/00 |
| | | | | 382/154 |
| 2015/0286786 | A1 | 10/2015 | El-Baz et al. | |
| 2016/0093085 | A1* | 3/2016 | Ray | A61B 5/6888 |
| | | | | 345/419 |
| 2016/0140721 | A1* | 5/2016 | Kawamura | G06T 7/593 |
| | | | | 382/132 |
| 2016/0210740 | A1* | 7/2016 | Ma | G06T 7/10 |
| 2017/0071671 | A1* | 3/2017 | Neumann | G16H 50/20 |
| 2017/0249423 | A1* | 8/2017 | Wang | G06V 10/7557 |
| 2018/0049695 | A1 | 2/2018 | Hector, Jr. | |
| 2018/0085080 | A1* | 3/2018 | Requardt | A61N 5/1039 |
| 2019/0388123 | A1* | 12/2019 | Pavlovskaia | A61B 90/37 |
| 2020/0160511 | A1* | 5/2020 | Lyman | G06N 20/00 |
| 2020/0271507 | A1* | 8/2020 | Sa | G16H 50/20 |
| 2021/0065394 | A1* | 3/2021 | Barnes | G06Q 30/0643 |

OTHER PUBLICATIONS

Xu et al., "Database-assisted low-dose CT image restoration", Feb. 28, 2013, Med. Phys. 40 (3) (Year: 2013).*
Song et al., "Categorization of lower body shapes for adult females based on multiple view analysis", 2011 (Year: 2011).*
Li et al., "Patient-specific biomechanical model as whole-body CT image registration tool", 2015 (Year: 2015).*
Wikipedia: "k-Means-Algorithmus"; 2018 [recherchiert am Jan. 27, 2021]: Im Internet: <URL: http://web.archive.org/web/20180907232613/ https://de.wikipedia.org/wiki/K-Means-Algorithmus.
Wang Yuxiu et al: "Fuzzy clustering analysis of body type in two-dimensional non-contacted body measurement system"; Journal of Textile Research; vol. 28; Issue 2; pp. 100-103; Feb. 28, 2007.

* cited by examiner

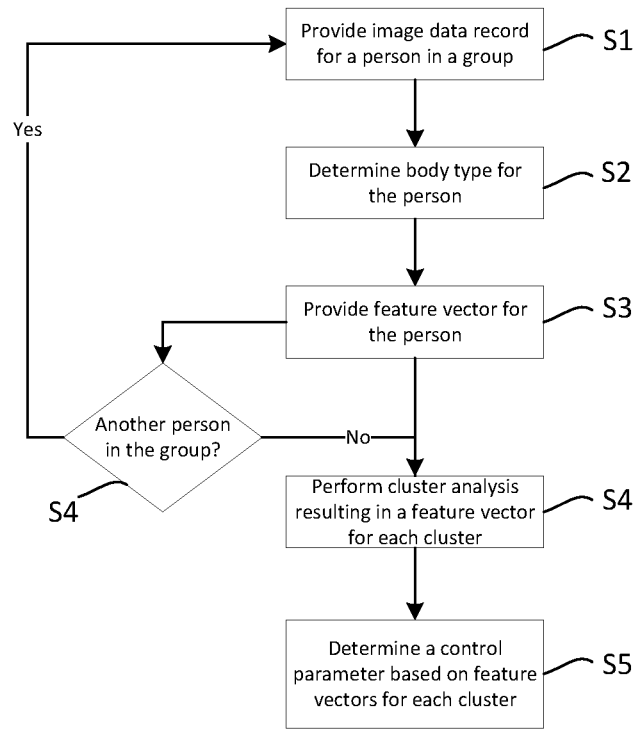
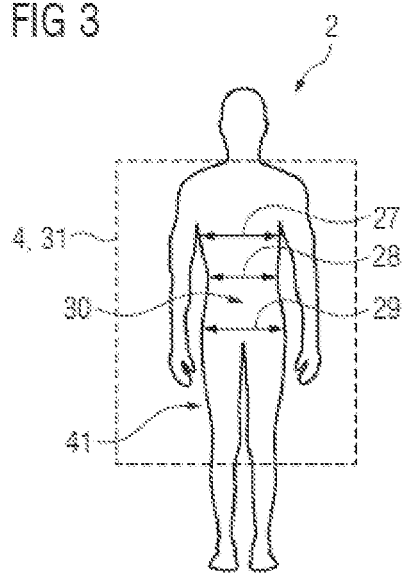

COMPUTER-IMPLEMENTED METHOD FOR CLASSIFYING A BODY TYPE

PRIORITY STATEMENT

The present application hereby claims priority under 35 U.S.C. § 119 to German patent application number DE 102020206232.3 filed May 18, 2020, the entire contents of which are hereby incorporated herein by reference.

FIELD

Example embodiments of the invention generally relate to a computer-implemented method for classifying a body type of at least one person, in particular at least one patient. In addition, example embodiments of the invention generally relate to a processing device, a computer program and a machine-readable data carrier.

BACKGROUND

For a plurality of, in particular medical, applications, it is advantageous to obtain an overview of the typical habitus, in other words the typical external appearance, of relevant groups of people or patients. In this regard, groups of people who use a specific clinic or who live in a specific region or a specific country may be of relevance, for instance. The habitus of a patient, in particular his size, his weight and his body type, in other words whether he is a patient with a rather small chest or with rather narrow hips, for instance, may be of relevance to the setting of operating parameters of a medical diagnostics device or therapy device, such as e.g. a radiation device or an imaging device, in particular e.g. for dose regulation within the context of x-ray recordings or for contrast agent administration. Within the context of a pre-configuration, it may be expedient here to predetermine preparatory parameters for a typical patient habitus in a specific clinic or for another restricted group of patients or to predetermine configurations for the setting of operating parameters of a medical diagnostics device or therapy device for the most relevant groups of people.

A distribution of the physical appearance in a patient base is typically not detected in detail.

It is therefore typically necessary to rely on estimations from large organizations, which, however, typically do not take into consideration regional influences or other influences which affect the individual patient base. Alternatively, a subjective estimation must be carried out, which is typically clearly prone to errors, however.

SUMMARY

The inventors have discovered that if the afore-cited disadvantages are to be avoided, it would be necessary to carry out a separate detection of corresponding data for every patient, which, however, results in additional work for medical personnel and in some instances may be prone to errors.

At least one embodiment of the invention therefore specifies an improved possibility of obtaining information relating to the body type and thus the habitus of individual people, and in the process also improves a detection of statistical information relating to larger groups.

Embodiments of the invention are described below both with reference to the method, the processing device and the computer program. Features, advantages or alternative embodiments mentioned herein are likewise also to be transferred to the other subject matters and vice versa. In other words, the object-based claims (which are directed at the processing device, for example) can also be developed with features described or claimed in connection with a method and vice versa. The corresponding functional features of the method are provided here by corresponding objective modules or subunits of the processing device or the computer program.

At least one embodiment of the invention is directed to a computer-implemented method for classifying a body type of at least one person, in particular at least one patient, which comprises:

receiving at least one image data record of the respective person, which maps at least one subarea of the person, and ascertaining a body type for the person by way of an optimization method, wherein a respective person model is used for each of the possible body types, said person model predetermining an expected person geometry of the person described by the person model as a function of a person parameter or of several person parameters, wherein the body type is selected by the optimization method, by a similarity measure for the similarity of the image data record or a person geometry ascertained from the image data record being optimized with the expected person geometry by selecting the body type.

In addition to at least one embodiment of the inventive method, the invention relates to a processing device, which is set up to carry out at least one embodiment of the inventive computer-implementing method. The data processing can take place by way of a correspondingly programmed microprocessor or FPGA, for instance. Alternatively, an implementation by a fixedly wired processing device, for instance an ASIC, is also possible. The processing device can comprise an input interface for receiving the at least one image data record as input data. Result data, for instance the body type, a feature vector or a group of characteristic feature vectors or also an item of control or configuration information for a dose control or contrast agent administration can be provided by way of an output interface. The processing device can be integrated into an imaging device or also embodied separately herefrom. For instance, the processing device can be a workstation computer or server or be implemented as a distributed solution, for instance as a cloud solution.

Moreover, at least one embodiment of the invention relates to a computer program for a processing device with program instructions, which carry out at least one embodiment of the inventive computer-implemented method when performed on the processing device.

In addition, at least one embodiment of the invention relates to a machine-readable data carrier, which comprises at least one embodiment of the inventive computer program.

Further, at least one embodiment of the invention relates to a computer-implemented method for classifying a body type of at least one person, comprising:

receiving at least one respective image data record of at least one respective person, the at least one image data record mapping at least one subarea of the respective person; and ascertaining a body type for the at least one respective person by an optimization method, wherein a respective person model is used for each of a respective possible body type, which as a function of at least one respective person parameter, provides an expected person geometry of the at least one respective person described by the respective person model, wherein the respective possible body type is selected by the optimization method by a similarity measure for similarity of the image data record or a person geometry determined from the image data record being optimized with the expected person geometry by selecting the body type.

Still further, at least one embodiment of the invention relates to a processing device, comprising at least one process, the at least one processor being configured to least:
receive at least one respective image data record of at least one respective person, the at least one image data record mapping at least one subarea of the respective person; and
ascertain a body type for the at least one respective person by an optimization method, wherein a respective person model is used for each of a respective possible body type, which as a function of at least one respective person parameter, provides an expected person geometry of the at least one respective person described by the respective person model, wherein the respective possible body type is selected by the optimization method by a similarity measure for similarity of the image data record or a person geometry determined from the image data record being optimized with the expected person geometry by selecting the body type.

Further, at least one embodiment of the invention relates to a non-transitory computer program product for a processor, storing program instructions, to carry out the computer-implemented method of an embodiment when carried out on the processor.

Even further, at least one embodiment of the invention relates to a non-transitory machine-readable data carrier, storing a computer program including program instructions, to carry out the computer-implemented method of an embodiment when carried out on a processor.

BRIEF DESCRIPTION OF THE DRAWINGS

Further advantages and details of the invention become apparent from the following example embodiments and the associated drawings. In this regard, shown schematically:

FIG. 2 shows a flow chart of an example embodiment of the inventive method, FIG. 3 shows an illustration to define body types in an example embodiment of the inventive method.

DETAILED DESCRIPTION OF THE EXAMPLE EMBODIMENTS

Figure 1:
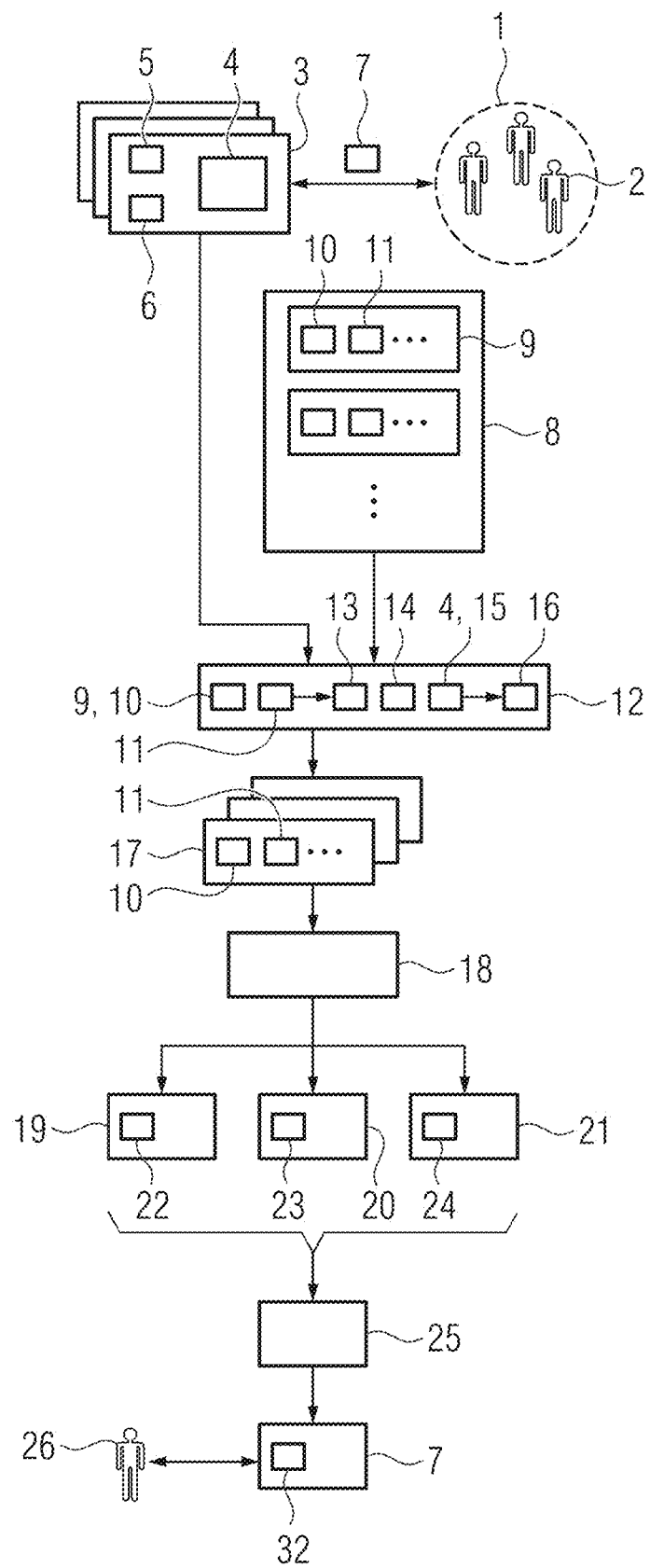
FIG. 1 shows data structures and algorithms used within the scope of an example embodiment of the inventive computer-implemented method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a computer-implemented method for classifying a body type of at least one person, in particular at least one patient, which comprises:

receiving at least one image data record of the respective person, which maps at least one subarea of the person, and ascertaining a body type for the person by way of an optimization method, wherein a respective person model is used for each of the possible body types, said person model predetermining an expected person geometry of the person described by the person model as a function of a person parameter or of several person parameters, wherein the body type is selected by the optimization method, by a similarity measure for the similarity of the image data record or a person geometry ascertained from the image data record being optimized with the expected person geometry by selecting the body type.

In particular, the body type of a person can be assigned to a plurality of categories of body types by way of a classification.

In at least one embodiment of the inventive method, use is made of image data records readily being frequently available for a significant part of the patient base or other groups of people, for instance topographic overview x-ray recordings or magnetic resonance tomography recordings, which map the entire person or at least sufficiently large subareas, in order to be able to conclude a body type.

Here a body type is understood to mean in particular different variations of the width or depth of the body along the height, in other words for instance the distinction as to whether the patient has rather wide hips and a small chest or vice versa and suchlike. Further parameters relating to the habitus, in particular the size and the weight of the person, can be considered here as person parameters.

It was recognized that the various body types can be effectively mapped by predetermining a person model parameterized by at least one person parameter for a respective body type. Within the scope of an optimization method, a decision can thus be made to determine which of the person models best matches the respective image data record and thus which body type most closely corresponds to the body type of the corresponding person. In the ideal case, here all further parameters upon which the image data record depends, in other words the person parameters and detection parameters relating to the imaging, would be known, so that it would be sufficient to compare the person geometry, predetermined by the respective person model during the corresponding parameterization, with the image data record or a person geometry ascertained herefrom and to simply select that body type for which an optimal similarity measure results. Depending on the selection of the similarity measure, an optimal similarity can result with a minimal or maximal similarity measure.

Typically not all parameters upon which the image data record depends are known, however. For instance, the relative position of the person with respect to a detection device can only be roughly known, a weight or a size of the person may be unknown or similar. In this case, the unknown parameters can be varied within the scope of the optimization method, in order to achieve an optimal similarity. Since in this regard relatively large parameter spaces can result, it may be advantageous not to scan the parameter space completely, but instead, for instance, to use a gradient descending method or suchlike within the scope of the optimization, in order to minimize or maximize a similarity measure.

Subsequent to determining the body type, the body type or an item of information determined herefrom can be provided by way of an output interface. The ascertained item of information can be a feature vector, for instance, which, in addition to the body type, comprises the at least one person parameter and is thus suited to at least largely characterizing the habitus of the respective person. If the method explained is carried out for very large groups of people, a very large number of feature vectors would result. It may therefore be advantageous to determine just a few particularly relevant feature vectors herefrom, for instance by way of a cluster analysis, such as is explained again later. Results of such an analysis can likewise be provided by way of an output interface.

As already mentioned above, the determination of the body type or the explained feature vector can also be used to control or preconfigure further procedures, in particular further imagings on other people. Control or configuration information can therefore also be provided by way of the output interface.

In at least one embodiment of the inventive method, the body type, as mentioned above, is to relate in particular to the physical shape of a person. Relatively simple person models, which relate exclusively to the physical shape of the person, can therefore be used. In particular, in the medical field, it may however also be advantageous to use what are known as atlases, which describe the anatomy of a respective person for a respective body type. This may be advantageous, for instance, if, within the scope of determining the body type or the person parameters, positions and/or sizes of internal features, in other words, for instance, a position and/or size of organs, bones etc., are to be taken into consideration.

At least one embodiment of the inventive method should determine in particular body types of larger groups of people. It is therefore advantageous if the image data, and in some instances, further additional information with respect to the person or the imaging, in other words in particular person and/or detection parameters, is extracted from a database. For instance, the DICOM format can be used, in which not only the image data itself, but instead in addition the recording or data relating to the person can be provided. A picture archiving and communication system (PACS) can be used as a data source, for instance.

It is typically assumed in the description which follows that the image data record involves two-dimensional x-ray data or a computed tomography. Other data sources for image data records, for instance magnetic resonance tomographs and cameras, can also be used, however.

With respect to the physical shape, it is possible to make a distinction between a rectangular, a triangular, an inverse triangular, a trapeziform and an oval body shape. With a rectangular body shape, the body of the person has approximately the same width in the region of the chest, hip and waist. With a triangular body shape, the width in the chest region is significantly smaller than in the hip region and the inverse applies with an inverse triangular shape. The trapezium shape corresponds to the inverse triangular shape to the extent that the upper region of the torso is wider than the lower region, wherein the waist and hips are less narrow than with the inverse triangular shape, however. The oval body shape is characterized by a round abdomen and round upper arms.

In at least one embodiment of the inventive method, all cited body shapes or only parts of these body shapes can be taken into consideration. It is also possible additionally to take further body shapes into consideration. For instance, an hourglass body shape can additionally be taken into consideration, which is a modification of the rectangular body shape with a narrower waist.

The respective person parameter can be determined within the scope of the optimization method. Alternatively or in addition, the respective person parameter can be received together with the respective image data record. If a number of person parameters are used, it is possible for all person parameters to be received, all person parameters to be determined within the scope of the optimization or parts of the person parameters to be received and the remaining person parameters to be determined within the scope of the optimization.

In cases in which a person parameter is received together with the respective image data record, within the scope of the optimization method the value of this person parameter can remain unchanged. It is however also possible to only use the received person parameter to predetermine a start value within the scope of the optimization or to predetermine limits within which the corresponding person parameter is varied within the optimization. Both a predetermination of the person parameter and also a determination within the scope of the optimization method enable a further variation of the body shape of the person to be mapped with a relatively small number of person models.

The size and/or the weight and/or the gender of the person and/or at least one variable which is dependent on the size and/or the weight can be used as person parameters. The size can be used in particular to scale the body model in the longitudinal direction. A scaling in the transverse direction and depth direction can take place based upon the weight. One of the known variables can be replaced for instance also by a variable which depends on size and weight, for instance by the body mass index. Since body shapes potentially differ significantly between genders, it may be advantageous with respect to the gender to define the person geometry forming part of a specific body type separately for the various genders and based upon the gender to select which of these geometries is to be used.

In the optimization method, the value of the similarity measure can additionally depend on at least one detection parameter, which relates to the detection of the respective image data record and which in each case is determined within the scope of the optimization method and/or is received together with the respective image data record. In this regard, the detection parameter can relate in particular to the recording geometry, in other words the position and/or orientation of the person with respect to the image or the detection volume. In this regard, the rough detection geometry can be provided together with the image data record, for instance an item of information which involves a front recording of the thorax, wherein within the scope of the optimization method the detection geometry can be varied in order to achieve improved matches.

Other detection parameters, in particular detection parameters relating to the dose in x-ray recordings, can be taken into consideration. For instance, with the use of the DICOM format, the so-called radiation dose structured report can be taken into consideration, in order to take into consideration the x-ray dose or the equivalent diameter. This can facilitate the segmentation of the body shape in the image data, for instance, or contribute to being able to better estimate a depth of the person at right angles to the image surface of two-dimensional image data based upon the developing absorptions.

At least one of the detection parameters can relate to a position and/or orientation of the person with respect to a detection device used to detect the image data record. This corresponds to the above-described position or orientation of the person with respect to the image or the detection volume.

The unknown or only roughly known person parameters or detection parameters can be determined in that a variation of the corresponding parameter is carried out within the scope of the optimization method. In the optimization method, the respective parameter is therefore determined together with the body type.

Alternatively, artificial intelligence methods or algorithms, in particular machine learning methods or algorithms, can also be used to determine at least one person parameter and/or at least one detection parameter. This may be advantageous, for instance, if only a relatively small section of a person is mapped, and a parameter relating to the entire person, for instance the weight, is to be determined. In order to enable this, a monitored learning can be used, for instance, in which training data records are used, which, in addition to the respective image data record, comprise the sought person parameter or detection parameter. Internal parameters of the training algorithm can then be varied in order, based upon the image data, to ascertain person parameters or detection parameters as input data, the latter matching as closely as possible with the predetermination of the training data. For this purpose, a back propagation of error can be used, for example.

Parameters of an artificial intelligence algorithm can generally be adjusted by training. In particular, machine learning methods for determining at least one person parameter and/or at least one detection parameter, monitored training, semi-monitored training, reinforcement learning and/or active learning can be used for the artificial intelligence method described here. Furthermore, representation learning (an alternative expression is "feature learning") can also be used. In particular, the parameters of an artificial intelligence algorithm can be adjusted iteratively by a number of training steps. The artificial intelligence algorithm can incidentally also be referred to as trained evaluation function.

The algorithm can in particular comprise a neural network, a support vector machine, a decision tree and/or a Bayesian network. The evaluation algorithm can also be based on k-means clustering, Q-learning, genetic algorithms and/or assignment rules. Within the scope of the present invention, the artificial intelligence evaluation algorithm preferably comprises a neural network. The neural network can be a deep neural network, a convolutional neural network (CNN) or a deep CNN. Furthermore, the neural network can be an adversarial network, a deep adversarial network and/or generative adversarial network (GAN). In particular, here neural networks can be understood to mean a series of layers, which represent abstractable intermediate steps, and can comprise an input layer and an output layer.

In at least one embodiment of the inventive method, the respective body type can be ascertained for all people in a group of people, wherein a feature vector, which comprises the body type and the person parameter or at least one of the person parameters as entries, is determined for each of the people and a cluster analysis of these feature vectors is carried out, by which the feature vectors are assigned to a fixedly predetermined number of clusters or a number of clusters determined within the scope of the cluster analysis, wherein a characteristic feature vector is determined for each of the clusters. The procedure described enables a relatively small number of characteristic feature vectors, for instance ten to twenty characteristic feature vectors, to be determined for a large number of people, for instance several hundred or several thousand or in some instances even a million or more people, said feature vectors describing specific avatars or archetypes, to which the large number of people can be assigned with typically good precision. In this regard it is typically advantageous to carry out the clustering under boundary conditions or to weight the distances between feature vectors so that a respective cluster essentially exclusively comprises a single body type.

A characteristic feature vector for a cluster of feature vectors can be formed, for instance, by the individual entries of the feature vector being considered in isolation and an average value or a median value being determined for each of these entries, for instance. It is also possible to select as a characteristic feature vector that one of the feature vectors for which the total of all distances of the further feature vectors in the cluster is minimal. Alternatively to selecting an existing feature vector, a feature vector can also be produced synthetically, for which the total of the distances of all feature vectors is minimal.

A partitioning cluster method, for instance a k-means algorithm, can be used in particular as a cluster analysis. The number of clusters to be formed can be fixedly predetermined. Alternatively, the known "elbow method" can be used, for instance, to determine a cluster number or similar.

For at least one further person, a further image data record can be recorded, wherein at least one control parameter, upon which the detection of the further image data record depends, in particular a used x-ray dose and/or contrast agent quantity, is predetermined as a function of the characteristic feature vectors. In other words, it is possible to take into consideration which person geometries typically occur in a specific patient base, in other words for instance in a specific hospital, a specific region or a town, and further image detections can be parameterized as a function of this in order to adjust the imaging as effectively as possible to the conditions on site.

As a function of the person parameter or the person parameters, the person model can predetermine an expected three-dimensional body surface of the person described by the person model as an expected person geometry. This is clearly advantageous when the image data record describes three-dimensional image data, since, in this case, a three-dimensional surface of the corresponding person can be determined and can be compared with the person model.

With the use of two-dimensional image data, the determination of a three-dimensional body surface as an expected person geometry may however also be advantageous, since misorientations of the person with respect to the detection device or the image or the detection volume can be easily recognized and corrected in this way. Moreover, it may also be possible, with x-ray recordings for instance, to take into consideration the dimensions of the patient at right angles to the image plane based upon the absorption.

One possibility for predetermining different person models for different body types is firstly to define a general model which has a relatively high number of parameters. For instance, a general model can firstly be used, which is formed by a number of layers stacked in the longitudinal direction of the person, for instance by 200 layers. The model parameters can relate in each case to the thickness and/or the expansion of the layer in depths and/or transverse direction of the person. If, for instance, an independent scaling is performed in each of these directions, one such general model has 600 parameters, wherein a plurality of parameter combinations clearly results in nonsensical body shapes. The person model for a specific body type can now be defined so that the parameter values of each of these many parameters are predetermined as a function of a relatively small number of person parameters, for instance as a function exclusively of the weight, the size and the gender.

The respective image data record can describe a two-dimensional x-ray recording, wherein the similarity measure depends on an expansion of the expected person geometry at right angles to the image plane of the two-dimensional x-ray recording and on an absorption strength of the x-ray radiation described by the x-ray recording by way of the person. This enables the depth of the person to be taken into consideration at right angles to the image plane, even if only two-dimensional image data exists. In this regard it is in particular possible to exclusively use regions of the image data record in which no significantly absorbing elements, for instance no bones, are arranged, so that tissue-independent absorption can be used as a basis, for instance.

The ascertained person geometry can be ascertained so that it describes a two-dimensional outline or a three-dimensional surface of the respective person or the mapped subarea of the respective person. The outline or the surface can be determined by known segmentation algorithms. In the simplest case, one such segmentation can take place by way of limit value comparison. A plurality of segmentation approaches for distinguishing between a person and surrounding air in the medical imaging data are known and are therefore not to be explained in detail.

In addition or alternatively to taking into consideration the surface or the outline of the person, it is also possible to take into consideration the positions and/or sizes of specific features, in other words, for instance, organs, bones and suchlike, in order to determine the determined person geometry.

An image data record of a two-dimensional x-ray image and/or a three-dimensional computed tomography examination and/or a magnetic resonance tomography examination and/or ultrasound measuring data and/or image data of a 3D camera can be used in each case as an image data record. 3D cameras can operate in the visible range or also in the infrared range. A stereo camera, an LIDAR, a time-of-flight sensor, a sensor based on structured light etc. can be used as a 3D camera.

In at least one embodiment of the inventive method, it is also possible for a number of image data records to be used for a person. These can be used together to ascertain the ascertained person geometry. This is expedient, for instance, if two-dimensional recordings exist from different angles or suchlike. In principle, it is also possible to separately ascertain a person geometry for the different image data records in each case, in order to carry out a consistency check, to reach a majority decision or suchlike.

In at least one embodiment of the inventive method, at least one operating parameter of a medical therapy device or a medical diagnostics device, in particular a radiation device or an imaging device, can be determined based upon the determination of the body type of the person.

In particular, the at least one operating parameter determined in this way can be transferred to the control unit of a medical therapy device or a medical diagnostics device, in order to adjust an operating protocol for a therapy application or a diagnostics examination to the respective person. In this way, a radiation protocol of a radiation device, a contrast agent injection protocol of a contrast agent injection device or a scan protocol of an imaging device can be adjusted in particular.

Within the context of at least one embodiment of the present invention, the radiation device can be in particular a device for radiation therapy with x-rays, gamma rays, electron beams or a particle therapy device.

Within the scope of at least one embodiment of the present invention, the imaging device can be in particular an x-ray device, for instance a computed tomography device, an ultrasound device or a magnetic resonance device.

In addition to at least one embodiment of the inventive method, the invention relates to a processing device, which is set up to carry out at least one embodiment of the inventive computer-implementing method. The data processing can take place by way of a correspondingly programmed microprocessor or FPGA, for instance. Alternatively, an implementation by a fixedly wired processing device, for instance an ASIC, is also possible. The processing device can comprise an input interface for receiving the at least one image data record as input data. Result data, for instance the body type, a feature vector or a group of characteristic feature vectors or also an item of control or configuration information for a dose control or contrast agent administration can be provided by way of an output interface. The processing device can be integrated into an imaging device or also embodied separately herefrom. For instance, the processing device can be a workstation computer or server or be implemented as a distributed solution, for instance as a cloud solution.

Moreover, at least one embodiment of the invention relates to a computer program for a processing device with program instructions, which carry out at least one embodiment of the inventive computer-implemented method when performed on the processing device.

In addition, at least one embodiment of the invention relates to a machine-readable data carrier, which comprises at least one embodiment of the inventive computer program.

Within the scope of a computer-implemented method, FIG. 1 shows algorithms and data structures used to classify a body type 10 of people 2, while FIG. 2 shows a flow chart of a corresponding method. The method can be used in particular to determine body types for a patient population, for instance in a hospital or in a specific region, and to control subsequent image recordings as a function hereof, for instance.

In the example embodiment shown, in steps S1 to S4, the respective body type 10 is firstly determined for the individual people 2 of the group of people 1 to be taken into consideration. In this regard, in step S1 at least one image data record 4 for one of the people 2 in the group of people 1 is firstly provided on the processing device 33 shown in FIG. 4, which is subsequently explained in further detail. The image data records 4 can be stored on a server 40, for instance, and provided by way of a network 39, such as is likewise shown in FIG. 4. In this regard, image data records 4 which have been detected by various detection devices 7, 7' can also be stored on the server 40, for instance. Alternatively or in addition, image data records 4 can also be provided directly by way of detection devices, as is shown schematically in FIG. 4 for the detection device 7". The individual image data records 4 can map the entire person 2. Typically, only a subregion 31 of the person 2, for instance the region of the torso in the image data record 4, is shown, as shown schematically in FIG. 3.

In the example shown, the image data records 4 are provided as part of a data structure 3, which may conform to the DICOM standard, for instance, and may comprise the additional values 5 for the person parameters 11, for instance for a weight, a size or a gender, and/or values 6 for detection parameters 14, for instance for a used radiation intensity, a used detection geometry, etc.

In step S2, a body type 10 is determined for the respective person 2. As was already explained in the general portion of the description, body types 10 can differ in particular in respect of the width progression of the person 2 along the body, in particular in the torso region. Shown schematically by way of example in FIG. 3 is a rectangular body type, for which the width 27 in the region of the chest, the width 28 in the region of the waist and the width 29 in the region of the hips is approximately equal, and no significant rounding appears in the region of the abdomen 30. With a triangular body type, the width 27 in the chest area would be considerably larger than the width 29 in the hip area, and with an inverse triangular type the inverse relationship would apply. With an oval body type, a significant rounding would appear in the region of the abdomen 30. Further body types were already discussed in the general part. It is significant here that the respective dimensions, in other words in particular the widths 27, 28, 29, do not result directly from the body type 10 but depend in addition on the person parameters 11, therefore, for instance, on the size, the weight and the gender of the person 2.

In order to ascertain the respective body type 10 of the person 2, a person model 9 is firstly predetermined for each possible body type 10, which is parameterized by at least one person parameter 11, preferably a number of person parameters 11. In the example shown, these person models 9 are stored in a database 8. Possibilities for predetermining and parameterizing such person models 9 were already discussed in detail in the general portion of the description and are therefore not repeated.

The determination of the body type 10 which is actually present with the person 2 is carried out by an optimization algorithm 12. In this regard, for improved understanding of the optimization algorithm 12, it is firstly assumed that values 5, 6 are provided for all person parameters 11 and detection parameters 14 to be take into account together with the image data record 4. Variants in which at least parts of these parameters are firstly determined within the scope of the optimization method 12 are then discussed.

Within the scope of the optimization method 12, the known values 5 for the person parameters 11 are firstly inserted into the person model 9 for each of the body types 10, in order to obtain an expected person geometry 13. The expected person geometry 13 can specify the expected three-dimensional shape of the surface of the respective person 2, for instance, if this has the corresponding body type 10.

This expected person geometry 13 is then compared with the image data record 4 or a person geometry 15 determined from the image data record 4, in order to determine a similarity measure 16. If the image data record 4 is a three-dimensional image data record, for instance, the three-dimensional shape of the surface of the person 2 can be determined as the determined person geometry by per se known segmentation algorithms, whereby the similarity measure 16 can be determined for instance as a deviation between the body surface 41 shown schematically in FIG. 3 and predetermined by the expected person geometry 13 and the three-dimensional shape predetermined by the ascertained person geometry 15.

If the image data record 4 involves by contrast two-dimensional x-ray data, an external outline of the person can be determined from this, for instance, and be compared with an outline for the expected person geometry 13 in order to determine the similarity measure. Since an absorption strength correlates with the depth of the body at right angles to the image plane at least in a large part of the body region, this absorption can additionally be taken into consideration and compared with an expected expansion at right angles to the image plane. In all the cases explained, typical distance measurements, for instance a two standard, can be used to determine a similarity measure from individual deviations.

In the previous discussion, it has been ignored that aspects of the image data record 4, in other words for instance the position of the person 2 with respect to the detection region and/or an x-ray intensity used within the scope of an x-ray recording, and thus the illumination intensity for individual pixels, depend on detection parameters 14, which were used by the detection device 7 within the scope of the imaging. Corresponding detection parameters 14 can be used, for instance, to register the expected person geometry 13 and the ascertained person geometry 15, to predetermine limit values or suchlike for a segmentation to ascertain the expected person geometry 15, to predetermine a correlation between an expansion of the expected person geometry 13 at right angles to the image plane and the absorption and suchlike.

If values 5, 6 are known for all person parameters 11 and detection parameters 14, the similarity measure 16, in the simplest case, can be determined for each of the body types 10 considered and the body type 10, for which the optimal similarity measure 16, in other words in particular a minimum or maximum for the similarity measure 16 results, can be determined as the body type 10.

In many applications, not all person parameters or not all detection parameters relating to the detection are known. For instance, the position of the respective person 2 with respect to the detection region is typically not known exactly and some person parameters, for instance the weight, may also be unknown. In this case, unknown parameters can be varied within the scope of the optimization method 12. An additional variation can also take place for person parameters or detection parameters for which the values 4, 5 are predetermined, said variation originating from the predetermined value, for instance, and only occurring about the predetermined value by way of a small interval.

In cases in which at least one person parameter and/or at least one detection parameter are determined within the scope of the optimization method 12, a large parameter space results overall, so that a determination of the similarity measure 16 would be very computationally intensive for every possible parameter value of the person and/or detection parameters 11, 14 and every body type 10. Typical optimization methods, for instance a gradient descending method, can therefore be used to optimize the similarity measure 16, for instance.

Once the optimization method 12 has completed, for instance if a convergence condition is fulfilled, the body type 10 ascertained and the person parameter 11 ascertained or provided in step S3 can be provided together as a respective feature vector 17. In step S4, a check is then carried out to determine whether a corresponding feature vector 17 has already been determined for each of the people 2 in the group of people 1 or for each data structure 3. If this is not the case, the method is repeated for the next person 2 from step S1.

As soon as feature vectors 17 are present for each of the people 2 in the group 1, in step S5 a cluster analysis 18 can be carried out, for instance by a k-means algorithm being applied to the feature vectors 17. In this regard, the number of clusters 19, 20, 21 to be formed can be fixedly predetermined, but it also possible, however, to ascertain an optimal cluster number, for instance by clusters being ascertained for different cluster numbers and an optimal cluster number being determined based upon the per se known elbow method. Methods for cluster analysis are known in principle in the prior art and require no further explanation here. A characteristic feature vector 22, 23, 24 is determined for each of the clusters 19, 20, 21, and can be selected, for instance, so that the distance of all feature vectors 17 in the respective cluster 19, 20, 21 from the characteristic feature vector 22, 23, 24 is minimal. Various approaches for this were already discussed in the general part and are not to be repeated.

The determination of the clusters 19, 20, 21 and the assigned characteristic feature vectors 22, 23, 24 is then primarily expedient if large groups of people 1 of people 2 are to be characterized, for instance if the group of people 1 comprises several hundred or several thousand people 2 or even more people 2, for instance a million people 2. By forming the clusters 19, 20, 21, people 2 with a similar habitus can be combined in one such cluster 19, 20, 21, and the associated characteristic feature vector 22, 23, 24 can form a typical habitus, in other words a type of archetype or avatar for this subgroup, which is combined in the cluster 19, 20, 21. Large populations of people, for instance populations of patients in large hospitals or entire regions, can therefore also be taken into consideration by a relatively small number of corresponding avatars or characteristic feature vectors 22, 23, 24. For the sake of clarity, only three clusters 19, 20, 21 are mapped, for instance. A good mapping of differently combined groups of people or patients is typically possible with ten to twenty clusters.

The characteristic feature vectors 22, 23, 24 ascertained in step S5 can be used in step S6 for instance to determine a control parameter 25, upon which the detection of a further image data record 32 by the or a further detection device 7 depends. The further image data record 32 can relate in particular to a person 26 who was not part of the group of people 1 originally considered. For instance, this can be a new patient in a hospital, the previous patient population of which is mapped according to the above-explained method by the characteristic feature vectors 22, 23, 24. Since it can typically be assumed that with new patients the distribution of the habitus corresponds to the distribution of the habitus with the already treated patients, it may be expedient to carry out a first parameterization of the image data detection based upon control parameters, which are ascertained as a function of the previous patient base or the characteristic feature vectors 22, 23, 24. The control parameter 25 can relate for instance to an x-ray dose or contrast agent quantity, which is used within the scope of the imaging.

Figure 4:
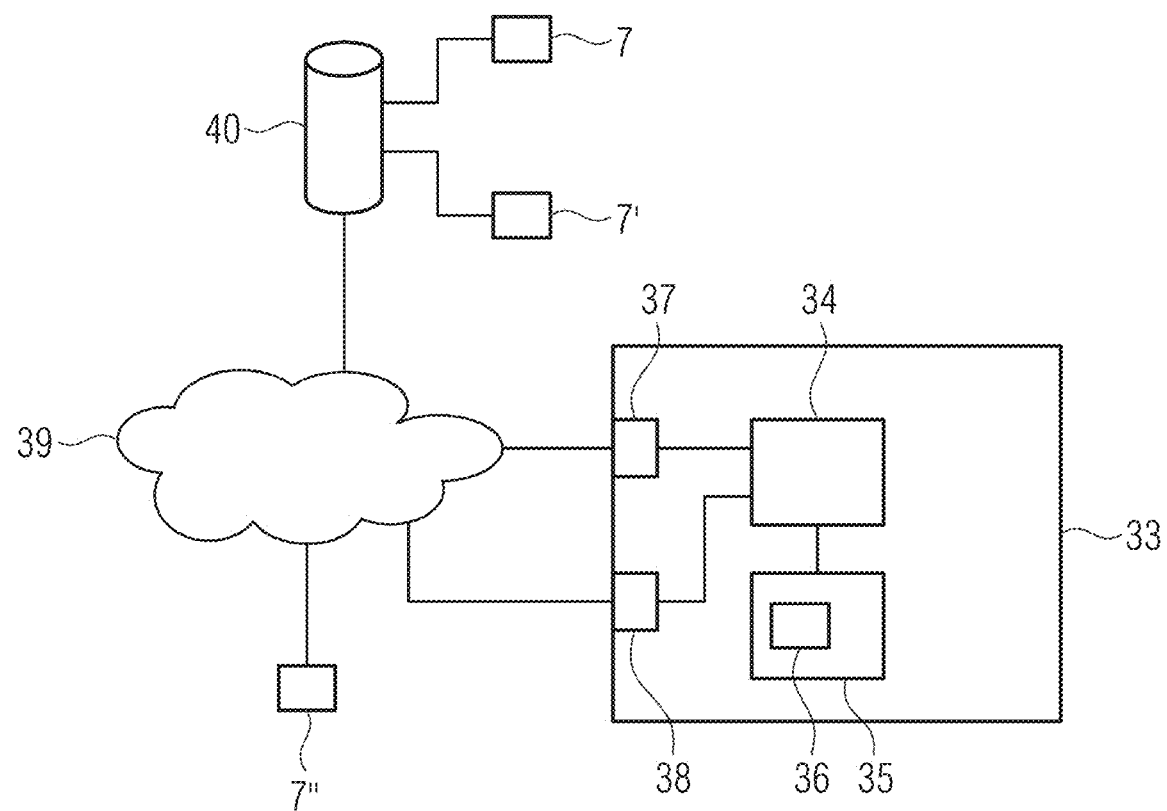
FIG. 4 shows an example embodiment of an inventive processing device and its communication partners.

FIG. 4 shows a schematic representation of an example embodiment of a processing device 33, which can be carried out by the method discussed above, and components interacting herewith. The processing device 33 can have a programmable processor 34 and an assigned memory 35, wherein a computer program 36, by way of which the afore-explained method is implemented, can be stored in the memory 35.

Input data, in other words in particular the image data records 4 or in general the data structures 3, can be received by way of an input interface 37 of the processing device 33. Output data, for instance the characteristic feature vectors 22, 23, 24, the control information 25 and/or feature vectors 17 of individual people 2 can be provided by way of an output interface 38. In the example, the input interface 37 and output interface 38 are coupled to further devices by way of a network 39, for instance the Internet. In this regard, for instance, a server 40 can provide image data records 4, which were detected by various medical image detection devices 7, 7'. Alternatively, an imaging device 7" can also provide directly corresponding image data, or be configured by the control parameter 25.

Although the invention has been illustrated and described in greater detail with the preferred example embodiment, the invention is not restricted by the examples disclosed and other variations can be derived therefrom by the person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for classifying a body type of at least one person, the computer-implemented method comprising:
   receiving at least one respective image data record of at least one respective person, the at least one respective image data record mapping at least one subarea of the at least one respective person; and
   ascertaining a body type for the at least one respective person by an optimization method, the body type being selected from a group of body types including a rectangular body shape, a triangular body shape, an inverse triangular body shape, a trapeziform body shape, an oval body shape, and an hourglass body shape, wherein a respective person model is defined for each possible body type of the group of body types, each respective person model providing an expected person geometry as a function of at least one person parameter,
   the body type is ascertained by the optimization method by
      inputting the at least one person parameter of the at least one respective person into each respective person model to obtain a set of expected person geometries, the set of expected person geometries including the expected person geometry of each possible body type of the group of body types,
      determining a similarity measure between the at least one respective image data record and the expected person geometry for each respective person model, and
      selecting the body type for the at least one respective person as the expected person geometry with a highest similarity measure to the at least one respective image data record,
   a respective body type is determined for all people in a group of people,
   each of a plurality of feature vectors, including the respective body type and the at least one person parameter as entries, is determined for each respective person and a cluster analysis of the plurality of feature vectors is carried out, by which the plurality of feature vectors are assigned to a fixed number of clusters or a number of clusters determined within a scope of the cluster analysis,
   a respective characteristic feature vector is determined for each respective cluster, and
   each respective cluster corresponds to a body type of the group of body types;
   determining at least one operating parameter of a medical therapy device or a medical diagnostics device based upon the body type of the at least one respective person;
   adjusting an operating protocol for a therapy application for the at least one respective person by transferring the at least one operating parameter to a control unit of the medical therapy device or the medical diagnostics device; and
   operating the medical therapy device or the medical diagnostics device to perform the therapy application based on the adjusted operating protocol.

2. The computer-implemented method of claim 1, wherein the at least one person parameter is at least one of
   determined in a scope of the optimization method, or
   received together with the at least one respective image data record.

3. The computer-implemented method of claim 2, wherein at least one of:
   at least one of size, weight or gender of the person is used as the at least one person parameter, or
   at least one variable, dependent upon the at least one of the size or the weight is used as the at least one person parameter.

4. The computer-implemented method of claim 2, wherein the similarity measure depends on at least one detection parameter, and wherein the at least one detection parameter at least one of
   relates to detection of the at least one respective image data record and respectively determined scope of the optimization method, or
   is received together with the at least one respective image data record.

5. The computer-implemented method of claim 4, wherein the at least one detection parameter relates to at least one of a position or orientation of the at least one respective person with respect to a detection device used to detect the at least one respective image data record.

6. The computer-implemented method of claim 1, wherein at least one of:
   at least one of size, weight or gender of the person is used as the at least one person parameter, or
   at least one variable, dependent upon the at least one of the size or the weight is used as the at least one person parameter.

7. The computer-implemented method of claim 1, wherein the similarity measure depends on at least one detection parameter, and wherein the at least one detection parameter at least one of
   relates to detection of the at least one respective image data record and respectively determined scope of the optimization method, or
   is received together with the at least one respective image data record.

8. The computer-implemented method of claim 7, wherein the at least one detection parameter relates to at least one of a position or orientation of the at least one respective person with respect to a detection device used to detect the at least one respective image data record.

9. The computer-implemented method of claim 1, wherein a further image data record is detected for at least one further person, and wherein at least one control parameter, upon which detection of the further image data record depends, is determined as a function of the respective characteristic feature vector for each respective cluster.

10. The computer-implemented method of claim 9, wherein the at least one control parameter is at least one of an x-ray dose or a contrast agent quantity.

11. The computer-implemented method of claim 1, wherein as the function of the at least one person parameter, the respective person model determines an expected three-dimensional body surface of the at least one respective person described by the respective person model as the expected person geometry.

12. The computer-implemented method of claim 1, wherein the at least one respective image data record describes a two-dimensional x-ray recording, and wherein the similarity measure depends on an expansion of the expected person geometry at right angles to an image plane of the two-dimensional x-ray recording and on an absorption intensity, described by x-ray detection, of x-ray radiation through the at least one respective person.

13. The computer-implemented method of claim 1, wherein the expected person geometry of the ascertained body type describes a two-dimensional outline or a three-dimensional surface of the at least one respective person or the at least one mapped subarea of the at least one respective person.

14. The computer-implemented method of claim 1, wherein at least one of an image data record of a two-dimensional x-ray image, an image data record of at least one of a three-dimensional computed tomography examination, a magnetic resonance tomography examination, ultrasound measuring data, or image data of a 3D camera is used as the at least one respective image data record.

15. A non-transitory computer program product for a processor, storing program instructions, to carry out the computer-implemented method of claim 1 when carried out on the processor.

16. A non-transitory machine-readable data carrier, storing a computer program including program instructions, to carry out the computer-implemented method of claim 1 when carried out on a processor.

17. The computer-implemented method of claim 1, wherein the medical therapy device or the medical diagnostics device is a radiation device or an imaging device.

18. The computer-implemented method of claim 1, wherein each of the respective characteristic feature vector for each respective cluster determines a control parameter used in a first parameterization of new image data.

19. A processing device of a medical therapy device or a medical diagnostics device, the processing device comprising:
at least one processor, the at least one processor being configured to at least cause the processing device to
receive at least one respective image data record of at least one respective person, the at least one respective image data record mapping at least one subarea of the at least one respective person; and
ascertain a body type for the at least one respective person by an optimization method, the body type being selected from a group of body types including a rectangular body shape, a triangular body shape, an inverse triangular body shape, a trapeziform body shape, an oval body shape, and an hourglass body shape, wherein
a respective person model is defined for each possible body type of the group of body types, each respective person model providing an expected person geometry as a function of at least one person parameter,
the body type is ascertained by the optimization method by
inputting the at least one person parameter of the at least one respective person into each respective person model to obtain a set of expected person geometries, the set of expected person geometries including the expected person geometry of each possible body type of the group of body types,
determining a similarity measure between the at least one respective image data record and the expected person geometry for each respective person model, and
selecting the body type for the at least one respective person as the expected person geometry with a highest similarity measure to the at least one respective image data record,
a respective body type is determined for all people in a group of people,
each of a plurality of feature vectors, including the respective body type and the at least one person parameter as entries, is determined for each respective person and a cluster analysis of the plurality of feature vectors is carried out, by which the plurality of feature vectors are assigned to a fixed number of clusters or a number of clusters determined within a scope of the cluster analysis,
a respective characteristic feature vector is determined for each respective cluster, and
each respective cluster corresponds to a body type of the group of body types,
determine at least one operating parameter of the medical therapy device or the medical diagnostics device based upon the body type of the at least one respective person;
adjust an operating protocol for a therapy application for the at least one respective person based on the at least one operating parameter; and
operating the medical therapy device or the medical diagnostics device to perform the therapy application based on the adjusted operating protocol.

* * * * *